(12) United States Patent
Guenther et al.

(10) Patent No.: US 7,648,401 B2
(45) Date of Patent: Jan. 19, 2010

(54) ELECTRODE LINE AND CONNECTING PIECE FOR ELECTROMEDICAL IMPLANTS

(75) Inventors: Thomas Guenther, Wilhelmshorst (DE); Klaus Bartels, Berlin (DE); Carsten Steglich, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 0 days.

(21) Appl. No.: 12/363,828

(22) Filed: Feb. 2, 2009

(65) Prior Publication Data

US 2009/0203258 A1 Aug. 13, 2009

(30) Foreign Application Priority Data

Feb. 13, 2008 (DE) ........................ 10 2008 008 927

(51) Int. Cl.
*H01R 24/04* (2006.01)

(52) U.S. Cl. ...................................... 439/669; 439/909

(58) Field of Classification Search .................. 439/668, 439/669, 909

See application file for complete search history.

(56) References Cited

U.S. PATENT DOCUMENTS

| | | | |
|---|---|---|---|
| 4,712,557 A * | 12/1987 | Harris | 607/37 |
| 5,060,649 A * | 10/1991 | Hocherl et al. | 607/37 |
| 5,458,629 A * | 10/1995 | Baudino et al. | 607/116 |
| 5,843,141 A * | 12/1998 | Bischoff et al. | 607/37 |
| 6,185,463 B1 * | 2/2001 | Baudino | 607/119 |
| 6,755,694 B2 * | 6/2004 | Ries et al. | 439/668 |
| 6,921,295 B2 * | 7/2005 | Sommer et al. | 439/668 |
| 7,047,627 B2 * | 5/2006 | Black et al. | 29/825 |
| 7,070,455 B2 * | 7/2006 | Balsells | 439/668 |
| 7,083,474 B1 * | 8/2006 | Fleck et al. | 439/668 |
| 7,191,017 B1 * | 3/2007 | Koop et al. | 607/122 |
| 7,195,523 B2 * | 3/2007 | Naviaux | 439/827 |
| 7,330,764 B2 * | 2/2008 | Swoyer et al. | 607/115 |
| 2003/0163171 A1 * | 8/2003 | Kast et al. | 607/36 |
| 2005/0182470 A1 | 8/2005 | Cross, Jr. | |
| 2005/0221671 A1 | 10/2005 | Lyu et al. | |
| 2008/0188919 A1 | 8/2008 | Bartels et al. | |

FOREIGN PATENT DOCUMENTS

EP 07023315.0 A2 8/2008

* cited by examiner

*Primary Examiner*—Ross N Gushi
(74) *Attorney, Agent, or Firm*—Craig A. Fieschko, Esq.; Dewitt Ross & Stevens, S.C.

(57) ABSTRACT

The invention relates to a connecting piece for connecting to an electrode line and to an electric implant, whereby the connecting piece has an electrically conducting plug module, multiple ring-shaped electrically conducting contacts with insulation sections having the same outside diameter arranged in the longitudinal direction therebetween, multiple electric connecting lines, and a supporting element which supports the insulation sections and secures them in the radial direction. A through-bore situated within the supporting element receives the plug module and/or a feeder line of an electrode body. The supporting element has grooves spaced along the longitudinal direction, and recesses extending from the proximal end to the distal end and running parallel to the longitudinal axis wherein the electric connecting lines are fit.

20 Claims, 5 Drawing Sheets

ELECTRODE LINE AND CONNECTING PIECE FOR ELECTROMEDICAL IMPLANTS

FIELD OF THE INVENTION

The invention relates to an electrode line for connection to electromedical implants such as a heart pacemaker, a cardioverter/defibrillator or a neurostimulator, for example, or a suitable combination thereof. The invention relates in particular to a connecting piece for such an electrode line.

BACKGROUND OF THE INVENTION

Electromedical implants of the aforementioned types are provided in various forms. Such implants usually have a tight housing comprising a power supply and other electronic and electric components to generate stimulation pulses and/or defibrillation shocks, and to deliver them over an elongated electrode line with a longitudinal axis to certain body sites, such as one or more chambers of the heart, a neural pathway, the spinal cord or the brain or to detect and process electronic potentials from these body parts. To this end, such implants are usually connected to electrode lines, which are inserted with a connecting piece on the proximal end of the electrode line into a bushing in a so-called header of the respective implant. The connecting piece and the bushing in the header of the implant have corresponding electrically conducting contacts to establish an electrically conductive connection between the heart stimulator and the electrode line.

In addition to a connecting piece on the proximal end, such electrode lines also comprise a tubular, flexible and bendable electrode body with a longitudinal axis and a distal end which faces the treatment location and at which the electrode poles by which the therapeutic and/or diagnostic signals are received or delivered are located. The electrode poles may assume the form of point electrodes on the distal end or ring electrodes in the vicinity of the distal end or large-area coil segments that serve to deliver shocks.

The electrode body has an electrically insulating outer shell, preferably biocompatible, in which the feeder lines are embedded to protect the feeder lines and insulate them with respect to the body tissue. The material of such a shell may be silicone, for example. In addition, another outer coating may be applied to the insulating outer shell; it may also be biocompatible, have a low coefficient of friction and facilitate the placement of the electrode line. Polyurethane, for example, meets these requirements for the outer coating.

The feeder lines described here serve to transmit measurement signals from the electrode poles to the connecting piece or to transmit stimulation pulses or defibrillation shocks from the connecting piece to the respective electrode poles. One or more of the feeder lines may have a coiled shape which runs within the outer shell. Through this coiled feeder line whose longitudinal axis is situated on the longitudinal axis of the electrode line, the electrode gains elastic properties, which prevent the electrode from breaking or the electric feeder lines from being damaged in the event of a possible mechanical tensile load. In addition, this coiled feeder line forms a lumen from the proximal end to the distal end of the electrode line along which the electrode can be guided on a guide wire or mandrel but through which therapeutic substances such as medicines may also be conveyed.

Furthermore, the electrode line has a kink guard at the transition to the connecting piece, preventing the connecting piece from developing a kink on the one hand while on the other hand serving as strain relief for joined contacts between the electrode feeder line and the connecting piece.

SUMMARY OF THE INVENTION

The present invention relates to the connecting piece on the proximal end of the electrode line and its connection to the other electrode lines.

The connecting piece in question here is of the type having several ring-shaped contacts of the same outside diameter and corresponding to the future standard IS-4. A variant of such a connecting piece is described in US 2005/0221671, for example, where a connecting piece for an electrode line for connection to an electric implant is disclosed, said implant having an elongated shape in a longitudinal direction and both a proximal end and a distal end. This connecting piece comprises an electrically conducting plug module, which protrudes proximally out of the proximal end of the connecting piece in the longitudinal direction.

In addition, the connecting piece comprises multiple ring-shaped electrically conducting contacts of the same outside diameter with insulation sections of the same outside diameter arranged between them in the longitudinal direction, where the insulation sections secure the electric contacts in such a way that their position in the longitudinal direction is invariable, the electric contacts each being connected to a corresponding electric feeder line of the electrode body.

Likewise, the connecting piece known from the state of the art comprises a supporting element with an essentially circular outside cross section and with a longitudinal axis along the longitudinal direction, which is designed to carry the insulation sections by means of protrusions and secure them in the radial direction and which has a through-bore on its longitudinal axis which accommodates the plug module and/or a feeder line of the electrode body.

The term "outside cross section" in the sense of this invention is understood to refer to the basic circle of a sheathing cylinder on which the outer edges or surfaces of the supporting element are situated. However, the outside cross section is not formed by the stop, which protrudes beyond the outside cross section.

Due to the protrusions in the supporting element according to the state of the art, which are situated in only one plane in the radial direction, however, it is impossible to reliably secure the insulation sections and the electrically conducting contacts in such a way that displacement in the radial direction is impossible. Tilting of the insulation sections away from the longitudinal direction/longitudinal axis is thus possible. Furthermore, economical prefabrication of the connecting piece is impossible because elements of the electrode body to whose proximal end the connecting piece is attached extend into the connecting piece to connect a plug module to an electrically conducting coil, for example.

European Patent Application 07023315.0 by the present applicant eliminates the aforementioned disadvantages and describes an electrode line having such a connecting piece, which has several ring-shaped electrically conducting contacts of the same outside diameter with insulation sections of the same outside diameter arranged between them in the longitudinal direction, the electrically conducting contacts of which are each in electric contact with an electrically conducting feeder line. The connecting piece disclosed here is assembled from several insulating intermediate pieces and electric contacts held by the former with connecting lines attached to them in the longitudinal direction of the connecting piece and sheathed with insulating plastic after being assembled.

However, this connecting piece has the disadvantage that the insulating intermediate pieces are on the inside. The injection compound arranged between the electrically conducting contacts due to the external sheathing cannot provide the required high-voltage dielectric strength which is why defective transmissions of signals, pulses or defibrillation shocks occur repeatedly.

Therefore, the invention preferably provides a connecting piece; an electrode line with such a connecting piece; and a method for producing such a connecting piece (as well as an electrode line with such a connecting piece), all of which reduce the disadvantages of the state of the art, allow production at a reasonable expense (e.g., by increasing the degree of preassembly), regardless of the type and number of contacts of the electrode line, and will ensure the required high-voltage dielectric strength.

The inventive connecting piece has a supporting element with n peripheral grooves with a space between them in the longitudinal direction, designed to receive an injection compound, and n recesses extending parallel to the longitudinal axis from the proximal end to the distal end to guide connecting lines from the electrically conducting contacts to the distal end, where n corresponds to the number of electrically conducting contacts.

The number "n" denotes a natural integer.

The electric connecting lines preferably protrude distally out of the distal end of the connecting piece to allow easy accessibility and a secure electric and mechanical connection to the electrode body.

This allows simple preassembly of the connecting piece because all the essential elements such as the electrically conducting contact faces and the insulation sections can be joined together by the injection compound. The required electric connection to the electrode body may be accomplished on the one hand by the connecting lines, which protrude distally on the distal end of the connecting piece to which the electrode body can be attached and are electrically connected to the electric lines of the electrode body. Secure mechanical attachment is accomplished through the insulating outer shell of the electrode body, which is mounted on and attached directly to the supporting element and at the same time serves as strain relief for the connection between the electric connecting lines of the connecting piece and the electric feeder lines of the electrode body.

The electrically conducting contacts and the insulation sections on the one hand and the supporting element on other hand preferably enclose an interior space into which, after the electrically conducting contacts, the insulation sections and the supporting element have been joined, the injection compound is introduced by injection molding, thereby joining the contacts, the insulation sections and the supporting element securely to one another.

The recesses running along the longitudinal axis are designed so that they are open radially to the outside along the entire supporting element. In other words, they are exposed before assembly so that the electric connecting lines can be introduced easily. After assembly, the recesses are covered by the ring-shaped electrically conducting contacts and the insulation sections, so that a closed channel is formed at least from the respective electrically conducting contact to the distal end, the connecting lines running in said channel, where they are protected from the respective contacts, to the distal end of the connecting piece. In addition, the connecting lines then run in these recesses with insulation. The supporting element is preferably made of a polymer, especially preferably of PEEK (polyether ether ketone), which is distributed by the Optima company under the brand name Victrex, or of PEKK (polyether ketone ketone), which is distributed by the company Oxford Performance Materials, Inc. under the brand name OXPEKK, or of POM (polyoxymethylene), which is distributed by the company Ticona under the brand name Hostaform, or even more preferably is made of ceramics, so this forms a complete insulating environment around the connecting line.

The borders of the recesses in the direction of the supporting element—i.e., in the direction of the longitudinal axis of the connecting piece—are designed so that, on the one hand, assembly from the outside is easily possible, and on the other hand, the connecting lines come to lie so securely that they do not slip during assembly. In addition, the shape depends on the number n of electrically conducting contacts and the same number of connecting lines. The borders of the recesses in the direction of the longitudinal axis are thus preferably bordered by secant surfaces, so that the supporting element has a body with a polyhedral cross section, preferably with an equilateral N-sided shape with an enveloping circle as the outside cross section. Three recesses with three secant surfaces are especially preferred. The borders of the recesses in the direction of the supporting element may, however, also assume other shapes, such as u-shaped or v-shaped borders, so that more than three connecting lines can lead to the distal end.

A polyhedron in the sense of the invention is an elongated body having a cross-sectional area with several segments arranged at angles, where the resulting edges and surfaces are bordered by the longitudinal axis of at most one enveloping circle as the outside cross section. According to the present invention, sections of the polyhedron may be formed by segments that are not straight but instead by enveloping circle segments which then form a fit for the electric insulation and/or electrically conducting contacts of the connecting piece.

The connecting piece may preferably be a supporting element with a peripheral stop on the distal end or in the vicinity thereof to allow accurate assembly of the electrically conducting contacts and insulation sections. By means of the stop, the contacts and insulation sections can be pushed in place and positioned in alternation, so that they can be preassembled in a standardized manner. The stop therefore has a recess which leads through the stop along the longitudinal axis. This recess may either be open further to the outside or may be formed by a bore through which the connecting lines are passed.

To simplify the injection of the injection compound and to permit a homogeneous distribution of the injection compound, the interior space enclosed by the electrically conducting contacts and the insulation sections on the one hand and the supporting element on the other hand is additionally formed by peripheral grooves and the recesses in the supporting element extending parallel to the longitudinal axis from the proximal end to the distal end. The recesses are joined to one another in this way and the injection compound can be introduced by means of an injection process. This leads to a more economical production process because the interior can be completely filled with casting compound in only one injection process. The injection compound may preferably consist of a single material, e.g., polyurethane, PEEK (polyether ether ketone) which is distributed under the brand name Victrex by the company Optima, PEKK (polyether ketone ketone), which is distributed under the brand name OXPEKK by the company Oxford Performance Materials Inc., or POM (polyoxymethylene), which is distributed under the brand name Hostaform by the company Ticona or more preferably is made of ceramics or especially preferably from the same materials as the supporting element. Alternatively, the injection compound may consist of at least two of the aforementioned materials.

The peripheral grooves are preferably arranged with a space between them, so that the ribs running in the longitudinal direction in front of and behind the grooves support the insulation sections and have an outside diameter that allows seating with an accurate fit for the respective insulation section. The ribs preferably have a width of 1 to 6 mm, especially preferably between 1.5 and 5.25 mm.

The plug module may preferably consist of a plug pin and a contact pin, which preferably has an elongated, rotationally symmetrical shape with a longitudinal axis which comes to lie on the longitudinal axis of the connecting piece. The plug pin serves to contact the electric implant and the contact pin serves to establish an electrically conducting connection to the feeder line of the electrode body. The plug pin is preferably fixedly secured on the contact pin by a welding method (e.g., by laser welding or resistance welding methods). On the distal end of the contact pin facing the electrode body, the contact pin has a recess along the longitudinal axis of the contact pin by means of which a feeder line of the electrode body—preferably shaped like a coil—can be fixedly attached. The fastening is preferably accomplished by a crimping process or by a welding process (for example, by laser jet welding or resistance welding).

The plug module preferably has an abutment, which is fixedly connected to the contact pin by means of one of the fastening methods mentioned above, for example. In addition, the supporting element has an inside thread at least on the proximal end into which a hollow screw can be screwed in the distal direction. When screwed in, this hollow screw prevents the plug module from being able to slip out of the connecting piece in the proximal direction by interacting with the abutment. The hollow screw is preferably a screw plug, which is situated closer to the proximal end of the connecting piece than the abutment on the plug module. The hollow screw has a bore whose diameter is adapted to the diameter of the contact pin, which has a smaller diameter than the abutment and the plug pin. The screw and the abutment therefore cooperate in such a way as to prevent the plug module from slipping out of the connecting piece in the proximal direction. The hollow screw cooperates with the plug pin in such a way that the plug module cannot slip in either the distal or proximal direction.

The advantage of this design is that the plug module can be inserted repeatedly into the plug bushing of the connection housing of an electric implant and removed again.

It is also advantageous that the plug module is freely rotatable about the longitudinal axis. This rotatable plug module is often needed with electrode lines which have a so-called active attachment on the distal end. The active attachment is usually embodied as a fastening coil, preferably as an attaching screw. To fasten this attachment screw in the cardiac tissue, a rotational movement must be executable. The electrode line as a whole cannot be rotated, which is why the plug module and the coiled feeder line attached to it are mounted so they can rotate about the longitudinal axis. The coiled feeder line is in turn connected to the active attachment. A rotary movement of the plug module thus produces the attachment in the cardiac tissue by driving the fastening coil out of the electrode and into the tissue.

In contrast with that, the plug module of an electrode line is not rotatably mounted with such a so-called passive attachment and instead is secured to prevent a rotational movement because this attachment is accomplished by stationary anchors (usually made of silicone) on the distal end by the fact that these anchors hook themselves in the trabecular meshwork of the ventricle.

The plug module also preferably has a through-bore along the longitudinal axis which, together with the lumen formed by the coiled feeder line of the electrode body, forms a continuous passage for a guide wire or a mandrel.

To prevent twisting of the plugs for certain types of electrode lines, the plug pin also preferably comprises a fixedly attached gripping device, which engages in the rotational slot on the screw and thus prevents it from turning. Cooperation of the engagement device with the rotational slot on the screw is ensured by the fact that the position of the plug pin is secured in the proximal direction by the cooperation between the hollow screw and the abutment just described.

Like all conducting materials in the connecting piece, the plug module is made of stainless steel such as medical stainless steel or MP35N, platinum-iridium alloys, tantalum, tantalum with a coating of a platinum-iridium alloy, Elgiloy or other implantable and conductive materials.

The invention also regards an electrode line for cardiac or neural use, having a longitudinal axis, a proximal end and a distal end facing the treatment site, comprising an inventive connecting piece at the proximal end as described above. The electrode line also has a flexible and bendable electrode body with an electrically insulating outer shell, which extends from the proximal end to the distal end of the electrode body, in which n electric feeder lines are embedded with electric insulation and an electric connection is established between the n electric connecting lines of the connecting piece with n electrode poles on the distal end. Likewise, a coiled feeder line, which is situated on the longitudinal axis of the electrode body within the outer shell and which establishes an electric connection between the electric plug module and an electrode pole on the distal end is also included. A kink guard establishes protection between the connecting piece and the electrode body, which is attached to the connecting piece.

The electric connection and simultaneous mechanical fastening between the electric connecting lines of the connecting piece and the embedded electric feeder lines of the electrode body is advantageously established by spring elements of an electrically conductive material which are attached to the electric connecting lines and also to the electric feeder lines, the spring elements preferably being crimpable and weldable wire coils, especially preferably double coils. This meets the requirements of fatigue strength. Accordingly, the spring element is crimped and/or welded at the connecting lines and the feeder lines, preferably by laser welding or resistance welding.

The embedded feeder lines and the coiled feeder line are preferably cables, especially preferably DTF cables.

The wire coils are preferably attached to the connecting lines and to the feeder lines by welding and crimping. The feeder lines, the spring elements as well as the electrode poles and the conducting materials in the connecting piece are preferably made of stainless steel such as medical stainless steel or MP35N, platinum-iridium alloys, tantalum, tantalum with a coating of a platinum-iridium alloy, Elgiloy or other implantable and conductive materials.

The kink guard of the electrode line is preferably a tube, also designed as a "hose nozzle," which engages on the stop on the connecting piece and is thereby secured. The stop on the connecting piece, which is formed by the supporting element, preferably has a larger outside diameter than the diameter of the ring contacts or the insulation sections and thus forms an outwardly protruding peripheral rib. The stop cooperates with a groove situated in the interior of the tube on the distal end. The groove is positioned in the tube in such a way that the tube section distally from the groove is shorter than the section proximally from the groove. The tube is pushed over the connecting piece at the end of the electrode production process, as described further below, so that the short tube section lies in the direction of the connecting piece. The groove engages with the stop when positioned correctly, so that the long proximal tube section is situated above the connection point of the connecting piece and thus forms a slip-proof kink guard.

Even more preferably, the tube is designed as a cloth tube in at least some sections. A cloth tube is understood according to the invention to be a tube in which a sheet of intersecting fibers, preferably intersecting one another essentially at a right angle and woven together, is embedded. The fibers may be made of polyester, preferably the Dacron distributed by the DuPont company, or polytetrafluoroethylene, preferably the Teflon distributed by the DuPont company.

In addition, the invention is described by a production process for a connecting piece described above, comprising the following sequence steps:
  welding the electric connecting lines to the electrically conducting contacts,
  pushing the electrically conducting contacts onto the supporting element up to the stop in alternation with the insulation sections and aligning each electric connecting line in one of the recesses,
  filling up the interior space bordered by the electrically conducting contacts and the insulation sections on the one hand and the supporting element on the other hand with an injection compound, and
  curing the injection compound.

It is advantageous that this method allows prefabrication of the connection without manufacturing the complete electrode line. An electric function test can therefore be performed on the connecting piece, and defectively produced connecting pieces can be identified before producing the complete electrode line. This saves labor time and materials, and thus costs.

In addition, an inventive electrode line is produced by the following method:
  connecting the contact pin to the coiled feeder line,
  pushing the connecting piece preassembled as described above onto the contact pin,
  attaching the contact pin to the connecting piece and welding the plug pin onto the contact pin,
  crimping and/or welding the spring elements onto the embedded feeder lines of the electrode body,
  pushing the flexible electrode body onto the coiled feeder line,
  pushing and welding and/or crimping the feeder element onto the electric connecting lines of the connecting piece, and
  pushing the kink guard and engaging the kink guard on the stop.

The connection of the contact pin to the coiled feeder line of the electrode body is accomplished by a crimping operation and/or a welding operation and attaching the contact pin to the connecting piece is accomplished by screwing in the hollow screw.

BRIEF DESCRIPTION OF THE DRAWINGS

In the following discussion, the connecting piece and the electrode line are illustrated by an exemplary version wherein.

DETAILED DESCRIPTION OF THE INVENTION

Figure 1:
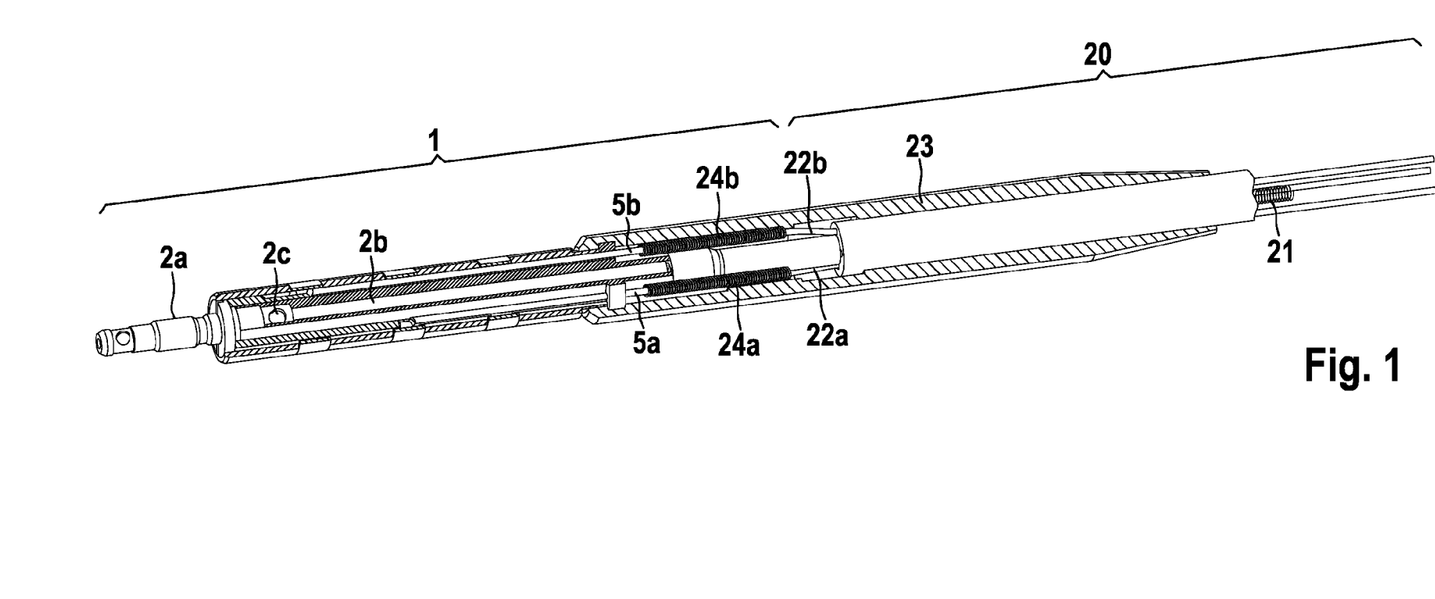
FIG. 1: shows a section of an electrode line with an inventive connecting piece.

FIG. 1 shows a section of the inventive electrode line. The electrode line comprises an inventive connecting piece 1, which is described further in the following text. In addition, the electrode line comprises a tubular, flexible and bendable electrode body 20 that extends along a longitudinal axis 100 (as shown in FIG. 2), a biocompatible, electrically insulating outer shell plus a distal end and a proximal end, whereby the proximal end is connected to the connecting piece 1. The distal end has a suitable securing means (not shown) with which the electrode line can be attached to the tissue, e.g., the heart, to allow electric pulses to be delivered. The attachment may be "active" or "passive" but with an active attachment on the distal end, a fastening coil is provided which must be attached actively by a rotational motion while a passive attachment usually has stationary anchors mostly made of silicone which become hooked in the tissue.

The electrode body 20 also comprises a coiled feeder line 21, which lies on the longitudinal axis 100. This feeder line 21 forms a recess, which also extends along the longitudinal axis 100 and is designed to receive a guide wire or other temporary guidance means. In the case of an actively securable electrode, this electric feeder line is rotatably mounted and is fixedly connected to the fastening coil on the distal end. Thus, by a rotational movement of the feeder line 21, the fastening coil can be activated and screwed into the tissue.

In addition, the electrode body comprises at least one feeder line 22a or 22b which is embedded in the outer shell and is insulated with respect to the outside and with respect to the coiled feeder line 21.

The coiled feeder line 21 and the at least one embedded feeder line 22a or 22b extend along the longitudinal axis 100 from the proximal end to the distal end, are electrically conducting and are connected at the proximal end to the connecting piece 1 and at the distal end to an electrode pole (not shown here). In the case of the coiled feeder line 21, the electrode pole may be the fastening coil.

In the transition area between the connecting piece 1 and the electrode body 20, there is a kink guard 23 for protection of the connection between the connecting piece and the electrode body.

For secure elastic electric connection of the embedded feeder lines 22a and 22b, each of these embedded feeder lines 22a and 22b is assigned spring elements 24a and 24b. These are preferably helical springs with a cavity, which are pushed over the feeder lines 22a and 22b. The spring elements 24a and 24b here protrude beyond the end of the feeder lines 22a and 22b in the proximal direction, so that on this end, electric connecting lines are also attached from the distal direction and secured there. By welding and/or crimping, the respective feeder lines 22a and 22b are electrically connected to the respective spring elements 24a and 24b, and the spring element is in turn electrically connected to the respective connecting line 5a and 5b. This ensures that the connection point between the connecting piece 1 and the electrode body 20 meets the requirements of fatigue strength.

The spring elements 24a and 24b are situated beneath the kink guard 23 and are protected by it.

The production process for such an electrode line comprises the following steps:

connecting the contact pin 2b to the coiled feeder line 21, pushing the preassembled connecting piece 1 onto the contact pin 2b, fastening the contact pin 2b onto the connecting piece 1 and welding the plug pin 2a onto the contact pin 2b, crimping and/or welding the spring elements 24a and 24b onto the embedded feeder lines 22a and 22b of the electrode body 20, pushing the flexible electrode body 20 onto the coiled feeder line 21, pushing and welding and/or crimping the spring element 24a and 24b onto the electric connecting lines 5a to 5c, and pushing the kink guard 23 into position and engaging the kink guard 23 on the stop 15.

The connection of the contact pin 2b to the coiled feeder line 21 of the electrode body 20 is accomplished by a crimping and/or welding operation, and the attachment of the contact pin 2b to the connecting piece 1 is accomplished by screwing in the hollow screw 16.

The inventive connecting piece is described below.

Figure 2:
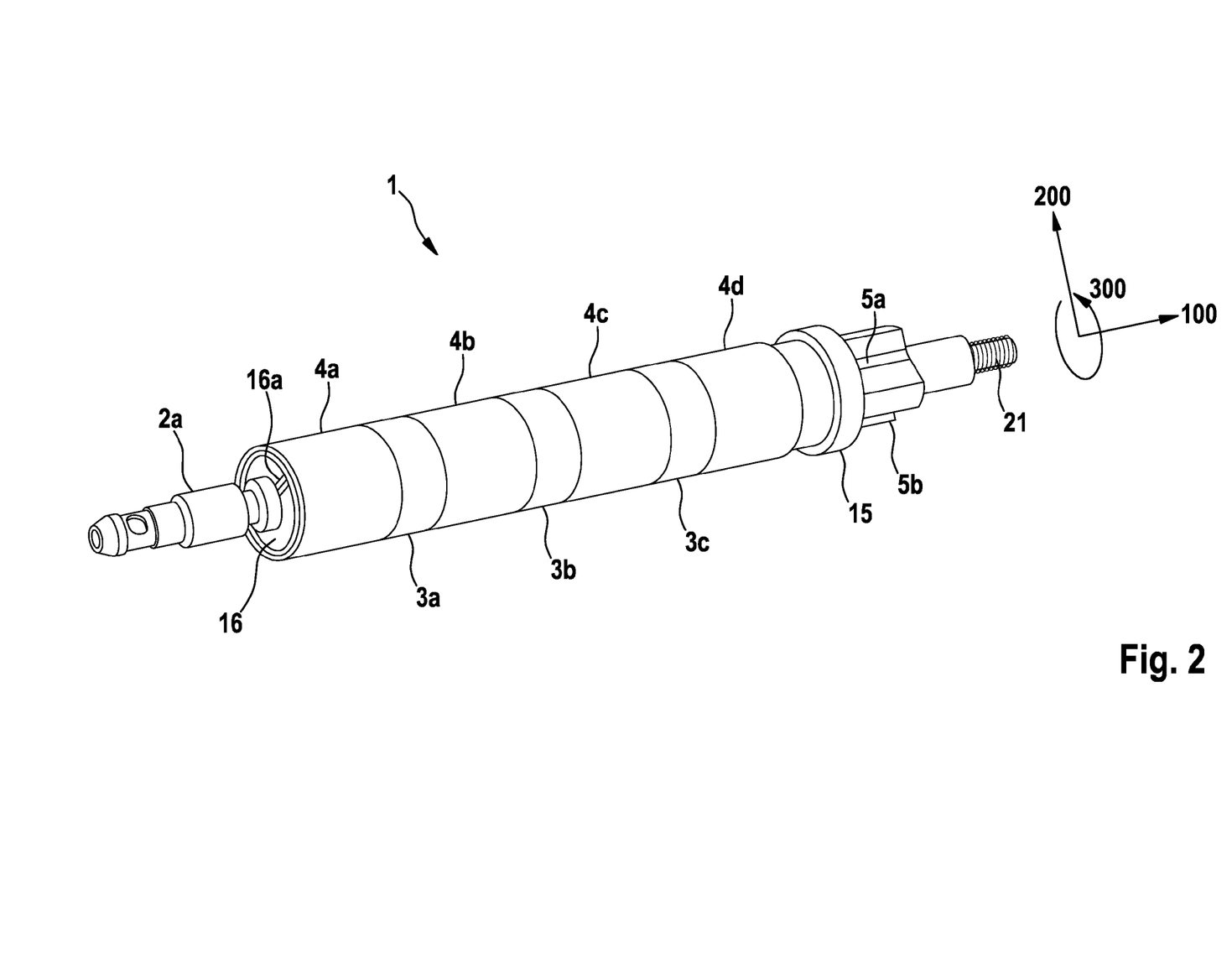
FIG. 2: shows the inventive connecting piece in a perspective diagram.

FIG. 2 illustrates a free-cut and independent four-pole IS-4 connecting piece 1 as illustrated in an outer view. This shows an IS-4 plug pin 2a which protrudes proximally out of the connecting piece 1 on the proximal end of the connecting piece 1. On the outside of the connecting piece 1, three electrically conducting contacts 3a, 3b and 3c in the form of ring contacts and insulation sections 4a to 4d are shown in alternation. The electrically conducting contacts 3a, 3b, and 3c and the insulation sections 4a, 4b, 4c, and 4d have the same outside diameter. In addition, a stop 15 is visible for attaching a kink guard 23 (not shown in FIG. 2). To more fully illustrate the mechanisms of action and the components, the following concepts are being introduced here: the longitudinal axis or the longitudinal direction 100 along which the connecting piece 1 is created, the radial axis or the radial direction 200 situated at a right angle to the longitudinal axis, along which displacement of the components is prevented by the supporting element 10 (FIG. 3), and the circumferential direction 300, which rotates about the longitudinal axis and along which the electric contact faces are located.

Figure 3:
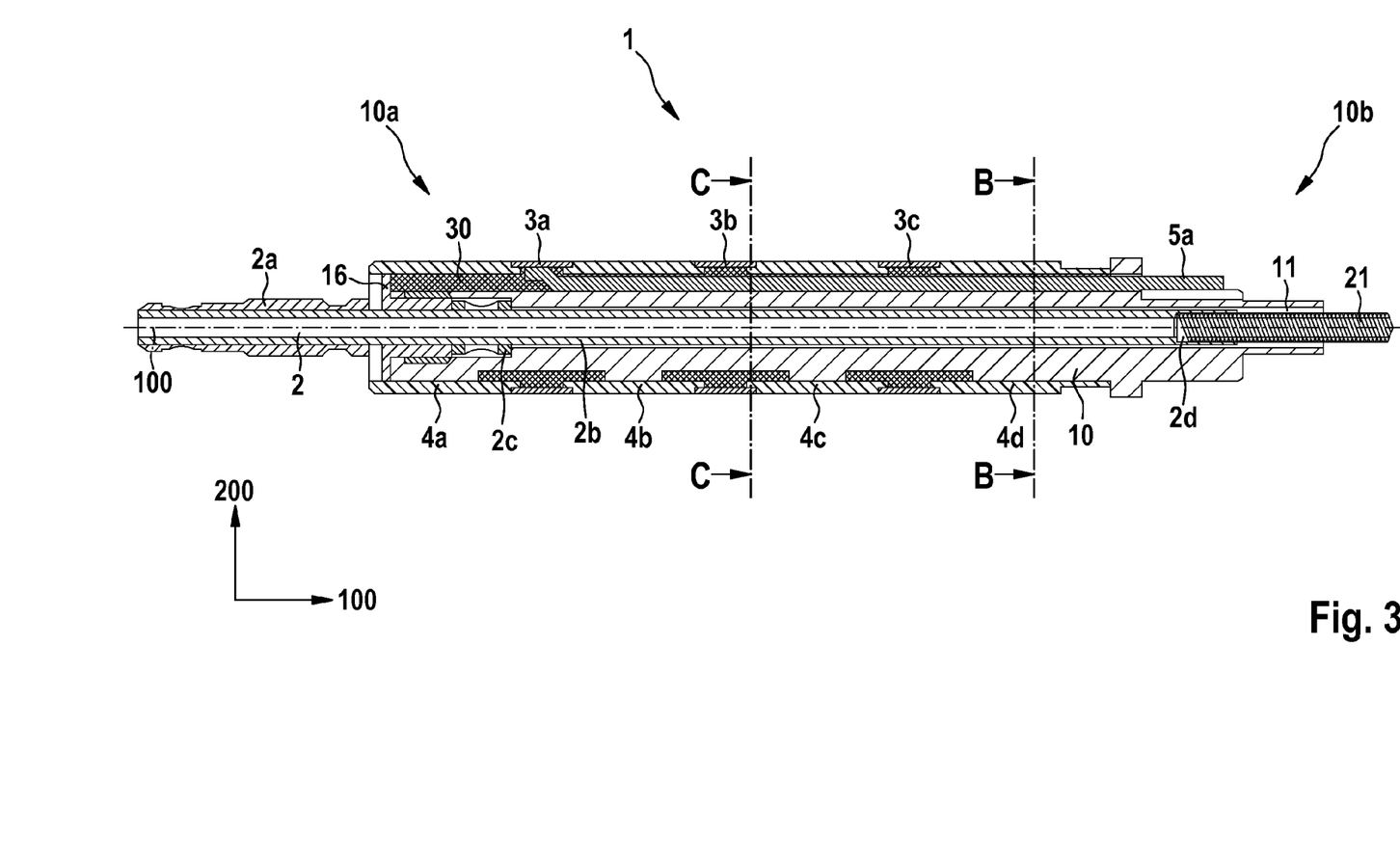
FIG. 3: shows the inventive connecting piece in a longitudinal section through the longitudinal axis, FIGS. 4a/4b/4c: show the inventive connecting piece in a side view with sectional lines B-B and C-C.

FIG. 3 shows the connecting piece 1 for a four-pole electrode line in a sectional diagram along the longitudinal axis 100. The connecting piece has been free-cut out of the electrode body 20 and is shown as an independent unit in a completely installed state.

The connecting piece 1 has an elongated shape along a longitudinal axis 100 and forms a proximal end 10a and a distal end 10b. A plug module 2 extends through almost the complete connecting piece 1 and protrudes proximally out of the connecting piece 1 at the proximal end 10a with a plug pin 2a, which in this embodiment is designed as a standardized IS-4 pin. The plug module 2 also comprises a contact pin 2b, to whose proximal end the plug pin 2a is fixedly attached by means of welding. On the distal end of the contact pin 2b, a coiled feeder line 21 of the electrode body 20 may be attached fixedly by crimping and/or welding. To do so, the contact pin 2b has a recess 2d into which the coiled feeder line 21 can be introduced and crimped or welded. The recess 2d advantageously serves to provide protection within the connecting piece 1. The contact pin 2b is mounted so it is initially freely rotatable about the longitudinal axis 100.

In addition, the connecting piece 1 has electrically conducting contacts 3a, 3b and 3c whose outside surface establishes an electric connection to the corresponding electrically conducting internal contacts in the connection housing (also called a header) of an electric implant. Thus the signals to and from the implant are relayed to the electrode poles of an electrode line. The electrically conducting contacts 3a, 3b and 3c are electrically insulated from one another by insulation sections 4a, 4b, 4c and 4d. This means that the electrically conducting contacts and the insulation sections alternate along the longitudinal axis 100, whereby the two insulation sections 4a and 4b situated between the contacts are identical, the insulation section 4a having a proximal covering edge to cover the connecting piece 1 proximally and the insulation section 4d has a recess running peripherally on the outside, designed to cooperate with a kink guard 23 (not shown). Each insulation section 4a, 4b, 4c, and 4d has shoulders on the side facing the electric contacts, said shoulders corresponding in their depth to the height of the electric contacts 3a, 3b, and 3c. The electric contacts 3a, 3b, and 3c come to lie on these shoulders and are thus secured by the insulation sections 4a, 4b, 4c, and 4d in the longitudinal direction 100, while the insulation sections are in turn secured by the supporting element 10 in the radial direction 200 and by the stop 15 in the longitudinal direction 100. In addition, this ensures that the electric contacts 3a, 3b, 3c and the insulation sections 4a, 4b, 4c and 4d have the same outside diameter in a standardized manner.

The insulation sections 4a to 4d, which are also ring shaped, are adjacent to the supporting element 10 on their inside surface, which is farther inward in the radial direction. This prevents the insulation sections 4a, 4b, 4c, and 4d from being displaceable in the radial direction.

The supporting element 10 has an essentially circular outside cross section and a longitudinal axis along the longitudinal direction 100 of the connecting piece 1. The supporting element 10 forms the complete length of the connecting piece 1 without the plug pin 2a. A through-bore 11 is provided on the longitudinal axis, designed to receive the plug module 2 and support it rotatably. The bore 11 has a recess on the proximal end 10a of the supporting element 10 and has an inside thread into which an abutment 2c can be inserted, said abutment 2c being fixedly connected to the contact pin 2b of the plug module 2. A hollow screw 16 having a through-bore with a diameter corresponding to the outside diameter of the contact pin 2b is inserted proximally from the abutment 2c. The abutment 2c cannot be moved in the proximal direction because it is blocked by the hollow screw 16. Thus the abutment 2c cooperates with the hollow screw 16 and prevents the contact pin 2b and thus the plug module 2 from being extractable proximally out of the connecting piece 1. In other words, the axial play may thus be minimized so that axial displacement is no longer possible when the hollow screw 16 has been screwed in. On the other hand, the hollow screw 16 also prevents the plug pin 2a, which also has an outside diameter greater than the inside diameter of the hollow screw 16, from being displaceable in the distal direction along the longitudinal axis. Due to this arrangement, a bearing which is rotatable along the longitudinal axis is obtained. To prevent this rotatability of the plug module 2, for example, an engagement device may be provided on the plug pin 2a, engaging in the rotational slot on the hollow screw 16, which thus prevents it from being rotatable.

FIG. 3 also shows that electrically conducting connecting lines are assigned to each electrically conducting contact 3a, 3b or 3c. This shows the connecting line 5a, which is connected electrically by a weld or solder connection to the electrically conducting contact 3a. The line 5a is guided in parallel to the longitudinal axis in the distal direction to be attached there electrically to feeder lines 22a/22b of an electrode body 20. The connecting lines 5b/5c of the other electrically conducting contacts 3b/3c are guided similarly and are situated so they are in recesses distributed around the longitudinal axis.

As also shown in FIG. 3, the supporting element 10 on the one hand and the electrically conducting contacts 3a, 3b, 3c and the insulation sections 4a to 4d on the other hand form an interior space that is filled with injection compound 30. The injection compound 30 consists of a single material, which preferably corresponds to the material of which the supporting element 10 is made. This is preferably PEKK. Due to this filled interior space in conjunction with the insulation sections 4a, 4b, 4c, and 4d, this connecting piece 1 meets the requirements of high-voltage strength and dielectric strength.

The connecting piece 1 is produced by a process that includes the following steps:
  welding the electric connecting lines 5a to 5c to the electrically conducting contacts 3a to 3c,
  pushing the electrically conducting contacts 3a, 3b, and 3c onto the supporting element 10 up to the stop 15 in alternation with the insulation sections 4a to 4d, and aligning each electric connecting line 5a, 5b, 5c in one of the recesses 13a to 13c,
  filling up the interior space bordered by the electrically conducting contacts 3a to 3c and the insulation sections 4a to 4d on the one hand and the supporting element 10 on the other hand with an injection compound 30, and
  curing the injection compound 30.

Figure 4A:
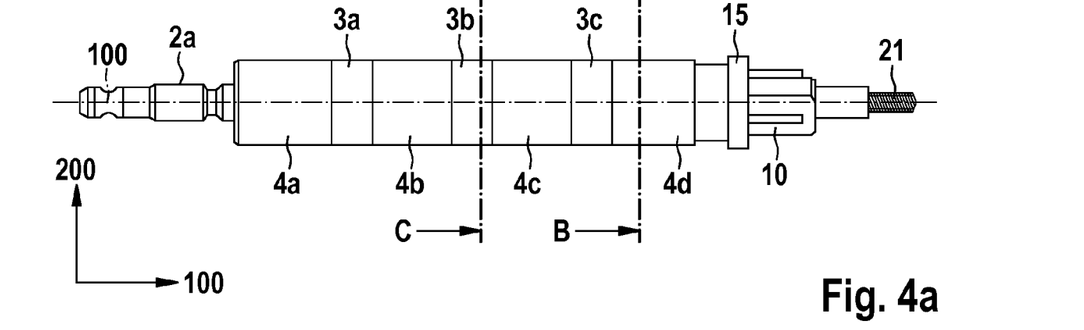
Figure 4B:
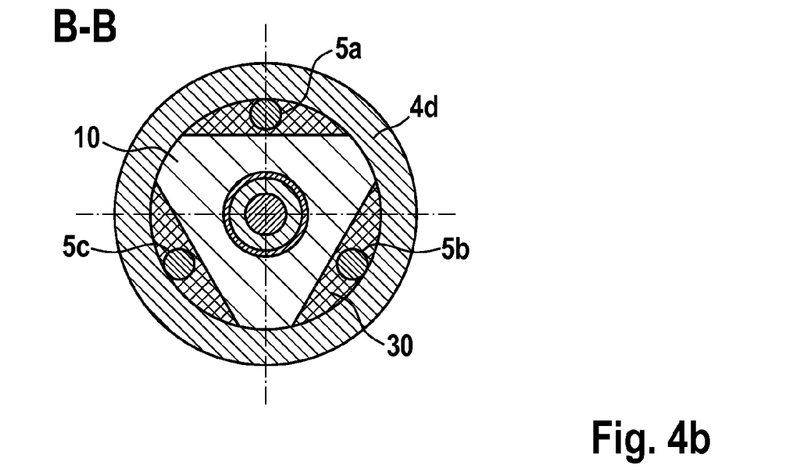
Figure 4C:
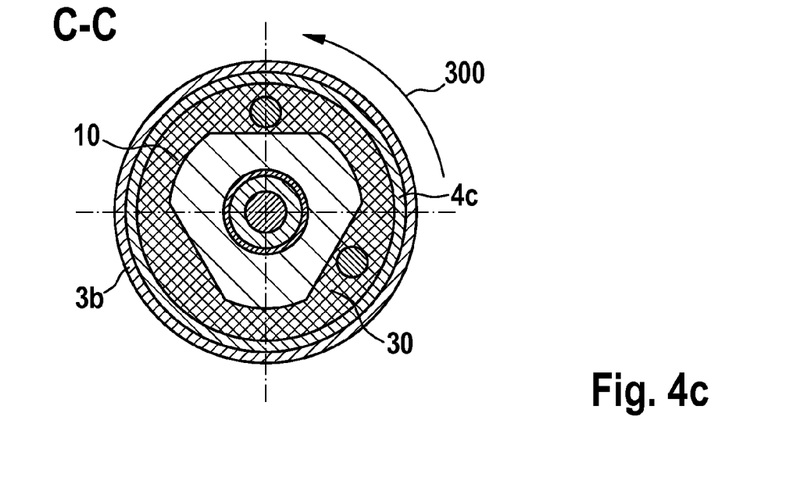

FIGS. 4a to 4c show a side view of a connecting piece 1 produced in this way, showing the electrically conducting contacts 3a to 3c, the insulation sections 4a to 4d, and parts of the supporting element 10. In this exemplary embodiment, a plug pin 2a is welded and/or crimped onto the proximal end of the contact pin and a helical feeder line 21 is welded and/or crimped onto the distal end of the contact pin (not visible here) on the inside. As an example, two sections are shown along sectional edges B-B (FIG. 4b) and C-C (FIG. 4c). These sections show the interior space between the electrically conducting contacts 3a, 3b, and 3c and the insulation sections 4a, 4b, 4c, and 4d on the one hand and on the other hand the supporting element 10, which is filled with an injection compound 30. The connecting lines 5a to 5c running in this interior space are situated on the supporting element 10 on one side and are sheathed with injection compound 30 on the other sides. This forms an optimal insulation, which ensures high-voltage strength and dielectric strength. In addition, the individual connecting lines 5a, 5b, 5c may be sheathed with an additional insulation layer to further optimize the aforementioned effect. It can also be seen that the insulation sections 4a, 4b, 4c 4d have a much greater extent in the radial direction 200 than the ring contacts 3a, 3b, and 3c. This has a further positive influence on the high-voltage strength and dielectric strength.

Figure 5:
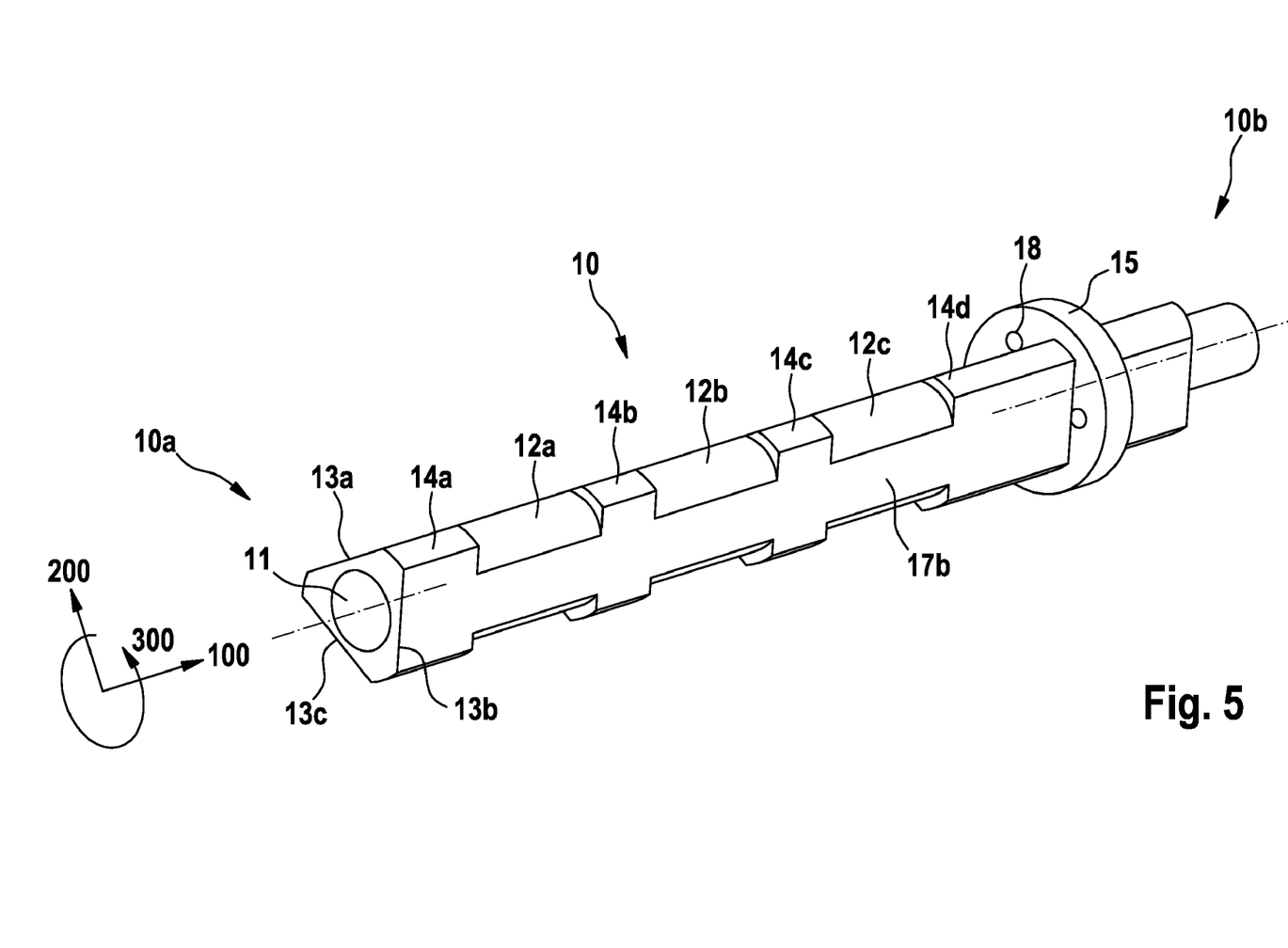
FIG. 5: shows the supporting element in a perspective view.

FIG. 5 shows the inventive supporting element 10 with an essentially circular outside cross section and with a longitudinal axis along the longitudinal direction 100. The supporting element 10 is designed to support the insulation sections 4a, 4b, 4c, 4d (not shown here) and to secure them in the radial direction 200. In addition, it has a through-bore 11 which is situated on its longitudinal axis and receives the electrically conducting contact pin 2b and/or a coiled feeder line 21 of the electrode body 20. The supporting element 10 has a recess on its proximal end 10a and an inside thread, where the recess has a larger diameter than the bore 11. As described further above, this recess is designed to receive an abutment 2c and a hollow screw 16.

The supporting element 10 shown here, which is provided for a connecting piece 1 with three conducting contacts 3a, 3b, 3c and one plug pin, has three peripheral grooves 12a to 12c which serve on the one hand to receive and distribute the injection compound 30 and on the other hand serve as a recess for the welding or solder contact between the electrically conducting contacts 3a, 3b, 3c and the connecting lines 5a, 5b, and 5c. The ring contacts 3a, 3b, 3c thus come to lie above the grooves 12a, 12b, 12c in the radial direction, while the insulating sections 4a, 4b, 4c are situated centrally on the ribs 14a to 14d. The outside diameter of the ribs 14a, 14b, 14c, 14d may be of such dimensions that it results in a fit with the inside diameter of the insulation sections 4a, 4b, 4c, 4d. This produces a more stable seating of the insulation sections 4a to 4d and the electrically conducting contacts 3a to 3c secured by them, and provides fixation in the radial direction 200. The ribs 14a to 14d preferably have a width of 1 to 6 mm and especially preferably between 1.5 and 5.25 mm.

In addition, three recesses 13a, 13b, 13c are provided, extending from the proximal end 10a to the distal end 10b, running parallel to the longitudinal axis 100. The connecting lines 5a, 5b, 5c (not shown) run in these recesses 13a, 13b, 13c from the respective electrically conducting contact 3a, 3b, 3c to which the connecting lines are connected at least to the distal end 10b, whereby the connecting lines 5a, 5b, 5c may protrude distally beyond the distal end 10b of the supporting element 10 to be better assembled with the feeder lines 22a, 22b, etc. of the electrode body. The number of grooves and the number of recesses correspond to the number of electrically conducting contacts.

Due to the number of electrically conducting contacts 3a, 3b, 3c, the shape of the recesses 13a, 13b, 13c running along the longitudinal axis 100 is also influenced significantly. With a smaller number of electrically conducting contacts 3a, 3b, 3c, the borders of the recesses 13a, 13b, 13c in the direction of the longitudinal axis 100 are of a superficial nature. Thus "secant surfaces" are formed on cylinders when the base area of the cylinder is cut by secants. FIG. 5 shows "secant surface" 17b which has essentially an identical shape to two other surfaces 17a and 17c, which are not visible here. The greater the number of recesses 13a, 13b, 13c, the more the area must be supplemented by a component radially, so that u-shaped or v-shaped borders are formed in the direction of the longitudinal axis. This assists the reliable guidance of the connecting lines. The cross section of the supporting element 10 thus assumes a "star shape" with an increase in the number of electrically conducting contacts 3a, 3b, 3c or assumes an N-sided shape, where the resulting edges and surfaces of the longitudinal axis 100 are bordered maximally by an enveloping circle as an outside diameter.

In the embodiment illustrated in FIG. 5, the outside surfaces of the ribs 14a to 14d are formed by sections of the enveloping circle and at the same time form the fit for the insulation sections 4a, 4b, 4c, 4d (which are not shown here).

On or near the distal end 10b, the supporting element 10 has a peripheral stop 15 having an outside diameter greater than the enveloping circle of the outside cross section of the remaining supporting element 10. This stop 15 serves first to facilitate assembly in preassembly of the connecting piece 1. The insulation section 4d (FIG. 2), which is not shown here, can thus be simply pushed from the proximal end 10a onto the supporting element 10 until it comes to lie against the stop 15. Then the electrically conducting contacts 3a to 3c (shown in FIG. 2) are pushed into place in alternation with the remaining insulation sections 4a to 4c (shown in FIG. 2)—after having been fixedly connected to the respective connecting line 5a to 5c (shown in FIG. 2), so that the electrically conducting contacts 3a, 3b, 3c come to lie on the shoulders of the insulation sections 4a, 4b, 4c, 4d. Due to this type of assembly, the electrically conducting contacts 3a, 3b, 3c are mounted in the location provided for them without having to provide tolerances. The connecting lines 5a, 5b, 5c are inserted into the respective recesses 13a to 13c in the interior space thereby formed in the direction of the distal end 10b, while being pushed into place, and through bores 18 situated distally from the recesses 13a to 13c, guided by the stop 15. Instead of forming this passage through the stop 15 by a bore 18 in the longitudinal direction, it is also possible for it to be formed by a recess that is open to the outside and is situated in the extension behind the recesses 13a to 13c. This has the advantage that the connecting lines 5a, 5b, 5c and thus the connecting piece 1 can be assembled even more easily.

On the other hand, the stop 15 works together with a groove on the kink guard 23, which is provided in the interior of the tube of the kink guard 23 at its distal end, i.e., the tube section distally from the groove is shorter than the section proximally from the groove. As described above, the kink guard 23 is pushed over the connecting piece 1 at the end of the electrode line production process, so that the short tube section of the kink guard 23 lies in the direction of the connecting piece 1. The groove engages with the stop 15 when correctly positioned, so that the proximal long tube section is situated above the connection point of the connecting piece on the electrode body and thus forms a slip-proof kink guard 23, which is situated above the spring elements 24a and 24b.

Preferred versions of the invention have been described above in order to illustrate how to make and use the invention. The invention is not intended to be limited to these versions, but rather is intended to be limited only by the claims set out below. Thus, the invention encompasses all different versions that fall literally or equivalently within the scope of these claims.

What is claimed is:

1. A connecting piece (1) for connection to an electrode line and an electric implant, the connecting piece (1) being elongated between a proximal end (10a) and a distal end (10b) and including:
    a. an electrically conducting plug module (2) which protrudes from the proximal end of the connecting piece (1),
    b. ring-shaped electrically conducting contacts (3a, 3b, 3c) having the same outer diameter,
    c. insulation sections (4a, 4b, 4c, 4d) spacing the contacts (3a, 3b, 3c) along the length of the connecting piece (1), the insulation sections (4a, 4b, 4c, 4d) having the same outside diameter, wherein the insulation sections (4a, 4b, 4c, 4d) secure the contacts (3a, 3b, 3c) against displacement along the length of the connecting piece (1),
    d. electric connecting lines (5a, 5b, 5c) extending between the contacts (3a, 3b, 3c) and the distal end (10b) of the connecting piece (1), and
    e. an elongated supporting element (10) having:
        (1) an outer diameter whereupon the insulation sections (4a, 4b, 4c, 4d) are situated,
        (2) an inner through-bore (11) wherein the plug module (2) is received,
        (3) circumferentially-extending peripheral grooves (12a, 12b, 12c) spaced along the length of the supporting element (10),
        (4) longitudinally-extending recesses (13a, 13b, 13c) spaced along the outer circumference of the supporting element (10), wherein the electric connecting lines (5a, 5b, 5c) are received within the recesses (13a, 13b, 13c).

2. The connecting piece (1) of claim 1 wherein a space is defined between:
    a. the contacts (3a, 3b, 3c) and the insulation sections (4a, 4b, 4c, 4d) on the one hand, and
    b. the supporting element (10) on the other hand, the space being filled by injection compound (30).

3. The connecting piece (1) of claim 2 wherein the electric connecting lines (5a, 5b, 5c) are at least partially embedded within the injection compound (30).

4. The connecting piece (1) of claim 1 wherein:
    a. spaced peripheral ribs (14a, 14b, 14c, 14d) are defined on opposing sides of the peripheral grooves (12a, 12b, 12c), and
    b. the insulation sections (4a, 4b, 4c, 4d) are each received on a respective one of the peripheral ribs (14a, 14b, 14c, 14d).

5. The connecting piece (1) of claim 1 wherein the recesses (13a, 13b, 13c) each define an at least substantially planar surface, whereby the supporting element (10) has a polyhedral cross section.

6. The connecting piece (1) of claim 1 wherein the supporting element (10) has a cross-section defined by an equilateral N-sided polyhedral shape wherein the corners of the shape are trimmed by an enveloping circle.

7. The connecting piece (1) of claim 1 wherein the supporting element (10) includes a peripheral stop (15) at or near the distal end, the peripheral stop (15) having a larger outer diameter than the adjacent proximally-situated portion of the supporting element (10).

8. The connecting piece (1) of claim 1 wherein the plug module (2) includes:
    a. a plug pin (2a) protruding from the proximal end of the connecting piece (1),
    b. a contact pin (2b) extending to the distal end of the connecting piece (1),
    c. an abutment (2c) on the contact pin (2b), the abutment defining an area of enlarged diameter on the contact pin (2b),
    d. a hollow screw (16) affixed to the supporting element (10), the hollow screw (16) being fit about the contact pin (2b) and against the abutment (2c) to secure the plug module (2) within the supporting element (10).

9. The connecting piece (1) of claim 1 further including:
    a. a flexible electrode body (20) having:
        (1) an electrically insulating outer shell extending between a proximal body end and a distal body end,
        (2) electric feeder lines (22a, 22b) extending within the shell, each electric feeder line (22a, 22b) being in connection with a respective electric connecting line (5a, 5b, 5c),
    b. at least one coiled feeder line (21) extending within the shell, the coiled feeder line (21) being in connection with the electric plug module (2).

10. The connecting piece (1) of claim 9 further including an elongated kink guard (23) extending over:
    a. at least a portion of the electrode body (20), and
    b. at least the distal end (10b) of the connecting piece (1).

11. The connecting piece (1) of claim 10 wherein:
    a. the supporting element (10) includes a peripheral stop (15) at or near the distal end, the peripheral stop (15) having a larger outer diameter than the adjacent proximally-situated portion of the supporting element (10), and
    b. the kink guard (23) is fit over the stop (15).

12. The connecting piece (1) of claim 9 wherein the electric connecting lines (5a, 5b, 5c) and the electric feeder lines (22a, 22b) are connected by spring elements (24a, 24b), the spring elements (24a, 24b) being fit over both the electric connecting lines (5a, 5b, 5c) and the electric feeder lines (22a, 22b).

13. A connecting piece (1) for connection to an electrode line and an electric implant, the connecting piece (1) including:
 a. an elongated supporting element (10) having:
  (1) grooves (12a, 12b, 12c):
   (a) spaced along the length of the supporting element (10), and
   (b) extending circumferentially about at least a portion of the supporting element (10),
  (2) recesses (13a, 13b, 13c):
   (a) spaced about the circumference of the supporting element (10) at angular intervals about the longitudinal axis (100) of the supporting element (10), and
   (b) extending between the grooves (12a, 12b, 12c) lengthwise along the circumference of the supporting element (10),
  (3) peripheral ribs (14a, 14b, 14c, 14d) defined by portions of the supporting element (10) longitudinally bounding the grooves (12a, 12b, 12c),
 b. electrically conducting contacts (3a, 3b, 3c) situated about the grooves (12a, 12b, 12c);
 c. electric connecting lines (5a, 5b, 5c) extending within the recesses (13a, 13b, 13c) and connecting to the contacts (3a, 3b, 3c).

14. A connecting piece (1) for connection to an electrode line and an electric implant, the connecting piece (1) including:
 a. an elongated supporting element (10) having:
  (1) recesses (13a, 13b, 13c):
   (a) extending alone the length of the supporting element (10), and
   (b) spaced at angular intervals about the longitudinal axis (100) of the supporting element (10),
  (2) grooves (12a, 12b, 12c):
   (a) spaced alone the length of the supporting element (10), and
   (b) extending circumferentially about at least a portion of the supporting element (10),
  (3) peripheral ribs (14a, 14b, 14c, 14d) defined by portions of the supporting element (10) longitudinally bounding the grooves (12a, 12b, 12c),
 b. electrically conducting contacts (3a, 3b, 3c) situated about the grooves (12a, 12b, 12c), wherein the contacts (3a, 3b, 3c) are embedded within injection compound (30) filling the recesses (13a, 13b, 13c),
 c. electric connecting lines (5a, 5b, 5c) extending within the recesses (13a, 13b, 13c) and connecting to the contacts (3a, 3b, 3c).

15. A connecting piece (1) for connection to an electrode line and an electric implant, the connecting piece (1) including:
 a. an elongated supporting element (10) having:
  (1) recesses (13a, 13b, 13c):
   (a) extending alone the length of the supporting element (10), and
   (b) spaced at angular intervals about the longitudinal axis (100) of the supporting element (10),
  (2) grooves (12a, 12b, 12c):
   (a) spaced alone the length of the supporting element (10), and
   (b) extending circumferentially about at least a portion of the supporting element (10),
  (3) peripheral ribs (14a, 14b, 14c, 14d) defined by portions of the supporting element (10) longitudinally bounding the grooves (12a, 12b, 12c),
 b. electrically conducting contacts (3a, 3b, 3c) situated about the grooves (12a, 12b, 12c),
 c. insulation sections (4a, 4b, 4c, 4d) situated adjacent the contacts (3a, 3b, 3c) along the length of the connecting piece (1), wherein the insulation sections (4a, 4b, 4c, 4d) engage the contacts (3a, 3b, 3c) to restrain them about the supporting element (10);
 d. electric connecting lines (5a, 5b, 5c) extending within the recesses (13a, 13b, 13c) and connecting to the contacts (3a, 3b, 3c).

16. A connecting piece (1) for connection to an electrode line and an electric implant, the connecting piece (1) including:
 a. an elongated supporting element (10) having:
  (1) recesses (13a, 13b, 13c):
   (a) extending alone the length of the supporting element (10), and
   (b) spaced at angular intervals about the longitudinal axis (100) of the supporting element (10),
  (2) grooves (12a, 12b, 12c):
   (a) spaced alone the length of the supporting element (10), and
   (b) extending circumferentially about at least a portion of the supporting element (10),
  (3) peripheral ribs (14a, 14b, 14c, 14d) defined by portions of the supporting element (10) longitudinally bounding the grooves (12a, 12b, 12c),
 b. electrically conducting contacts (3a, 3b, 3c) situated about the grooves (12a, 12b, 12c),
 c. insulation sections (4a, 4b, 4c, 4d) situated adjacent the contacts (3a, 3b, 3c) along the length of the connecting piece (1), and
 d. electric connecting lines (5a, 5b, 5c) extending within the recesses (13a, 13b, 13c) and connecting to the contacts (3a, 3b, 3c),
 wherein the insulation sections (4a, 4b, 4c, 4d) and contacts (3a, 3b, 3c) define an outer tubular shell about the supporting element (10), and
 wherein the recesses (13a, 13b, 13c) and grooves (12a, 12b, 12c) between:
  (1) the contacts (3a, 3b, 3c) and the insulation sections (4a, 4b, 4c, 4d) on the one hand, and
  (2) the supporting element (10) on the other hand, are filled by an injection compound (30).

17. A connecting piece (1) for connection to an electrode line and an electric implant, the connecting piece (1) including:
 a. an elongated supporting element (10) having:
  (1) recesses (13a, 13b, 13c):
   (a) extending alone the length of the supporting element (10), and
   (b) spaced at angular intervals about the longitudinal axis (100) of the supporting element (10),
  (2) grooves (12a, 12b, 12c):
   (a) spaced alone the length of the supporting element (10), and
   (b) extending circumferentially about at least a portion of the supporting element (10),
  (3) peripheral ribs (14a, 14b, 14c, 14d) defined by portions of the supporting element (10) longitudinally bounding the grooves (12a, 12b, 12c),
 b. electrically conducting contacts (3a, 3b, 3c) situated about the grooves (12a, 12b, 12c), and
 c. electric connecting lines (5a, 5b, 5c) extending within the recesses (13a, 13b, 13c) and connecting to the contacts (3a, 3b, 3c),
 wherein the recesses (13a, 13b, 13c) and grooves (12a, 12b, 12c) are covered with an integral layer of injection compound (30), with the injection compound (30) and the peripheral ribs (14*a*, 14*b*, 14*c*, 14*d*) defining an at least substantially cylindrical surface about the supporting element (10), 18. A connecting piece (1) for connection to an electrode line and an electric implant, the connecting piece (1) including:
   a. an elongated supporting element (10) having:
      (1) recesses (13*a*, 13*b*, 13*c*):
         (a) extending alone the length of the supporting element (10), and
         (b) spaced at angular intervals about the longitudinal axis (100) of the supporting element (10),
      (2) grooves (12*a*, 12*b*, 12*c*):
         (a) spaced alone the length of the supporting element (10), and
         (b) extending circumferentially about at least a portion of the supporting element (10),
      (3) peripheral ribs (14*a*, 14*b*, 14*c*, 14*d*) defined by portions of the supporting element (10) longitudinally bounding the grooves (12*a*, 12*b*, 12*c*),
   b. electrically conducting contacts (3*a*, 3*b*, 3*c*) situated about the grooves (12*a*, 12*b*, 12*c*),
   c. electric connecting lines (5*a*, 5*b*, 5*c*) extending within the recesses (13*a*, 13*b*, 13*c*) and connecting to the contacts (3*a*, 3*b*, 3*c*), and
   d. a flexible electrode body (20) having:
      (1) an elongated kink guard (23) extending over at least a distal end (10*b*) of the supporting element (10);
      (2) electric feeder lines (22*a*, 22*b*) extending within the kink guard (23), the electric feeder lines (22*a*, 22*b*) being in connection with the electric connecting lines (5*a*, 5*b*, 5*c*).

19. A connecting piece (1) for connection to an electrode line and an electric implant, the connecting piece (1) including:
   a. an elongated supporting element (10) having:
      (1) recesses (13*a*, 13*b*, 13*c*):
         (a) extending alone the length of the supporting element (10), and
         (b) spaced at angular intervals about the longitudinal axis (100) of the supporting element (10),
      (2) grooves (12*a*, 12*b*, 12*c*):
         (a) spaced alone the length of the supporting element (10), and
         (b) extending circumferentially about at least a portion of the supporting element (10),
         (3) peripheral ribs (14*a*, 14*b*, 14*c*, 14*d*) defined by portions of the supporting element (10) longitudinally bounding the grooves (12*a*, 12*b*, 12*c*),
   b. electrically conducting contacts (3*a*, 3*b*, 3*c*) situated about the grooves (12*a*, 12*b*, 12*c*),
   c. electric connecting lines (5*a*, 5*b*, 5*c*) extending within the recesses (13*a*, 13*b*, 13*c*) and connecting to the contacts (3*a*, 3*b*, 3*c*), and
   d. insulation sections (4*a*, 4*b*, 4*c*, 4*d*) situated adjacent the contacts (3*a*, 3*b*, 3*c*) along the length of the connecting piece (1),
   wherein both the contacts (3*a*, 3*b*, 3*c*) and the insulation sections (4*a*, 4*b*, 4*c*, 4*d*) are hollow.

20. A method for producing the connecting piece (1) of claim 19 including the following steps:
   a. affixing the electric connecting lines (5*a*, 5*b*, 5*c*) to the electrically conducting contacts (3*a*, 3*b*, 3*c*) in conductive communication;
   b. pushing the electrically conducting contacts (3*a*, 3*b*, 3*c*) over the supporting element (10) in alternation with the insulation sections (4*a*, 4*b*, 4*c*, 4*d*), with each electric connecting line being situated in one of the recesses (13*a*, 13*b*, 13*c*);
   c. filling up the interior space bordered by:
      (1) the electrically conducting contacts (3*a*, 3*b*, 3*c*) and the insulation sections (4*a*, 4*b*, 4*c*, 4*d*) on the one hand, and
      (2) the supporting element (10) on the other hand, with an injection compound (30).

* * * * *